(12) United States Patent
Bialecki et al.

(10) Patent No.: US 7,368,461 B2
(45) Date of Patent: May 6, 2008

(54) COMPOUNDS AND METHOD FOR THE TREATMENT OF OVERACTIVE BLADDER

(75) Inventors: Russell Bialecki, Wilmington, DE (US); Cathy Dantzman, Wilmington, DE (US); Keith Herzog, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 474 days.

(21) Appl. No.: 10/494,195

(22) PCT Filed: Nov. 1, 2002

(86) PCT No.: PCT/SE02/01991

§ 371 (c)(1),
(2), (4) Date: Apr. 30, 2004

(87) PCT Pub. No.: WO03/037889

PCT Pub. Date: May 8, 2003

(65) Prior Publication Data

US 2005/0203113 A1    Sep. 15, 2005

(30) Foreign Application Priority Data

Nov. 2, 2001 (SE) .................................. 0103795

(51) Int. Cl.
*A61K 31/4545* (2006.01)
*C07D 401/04* (2006.01)

(52) U.S. Cl. .................. 514/316; 546/190; 546/191

(58) Field of Classification Search ................ 514/316; 546/190, 191
See application file for complete search history.

(56) References Cited

U.S. PATENT DOCUMENTS

| | | | | |
|---|---|---|---|---|
| 5,559,131 A | * | 9/1996 | Miller | 514/329 |
| 5,576,333 A | | 11/1996 | Miller | |
| 5,677,317 A | * | 10/1997 | Miller | 514/316 |
| 5,731,309 A | * | 3/1998 | Bernstein et al. | 514/227.8 |
| 6,008,223 A | | 12/1999 | Bernstein et al. | |

FOREIGN PATENT DOCUMENTS

| | | |
|---|---|---|
| EP | 0630887 A1 | 12/1994 |
| WO | WO 9505377 A1 | 2/1995 |
| WO | WO 9628158 A1 | 9/1996 |
| WO | WO 0020003 A1 | 4/2000 |
| WO | WO 0025766 A2 | 5/2000 |
| WO | WO 0034243 A1 | 6/2000 |
| WO | WO 0197811 A1 | 12/2001 |

OTHER PUBLICATIONS

Miller et al. "4-carboxoamidopiperidine . . . " CA 122:105675 (1995).*
Miller et al. "Novel 4-piperidinyl . . . " CA 123:143649 (1995).*
Bernstein et al. "Preparation of 4-piperidinobutylamine . . . " CA 125:58328 (1996).*
Miller et al. "Preparation of N-piperidinoalkylbenzamides . . . " CA 126:47105 (1996).*
King "Bioisosteres, conformational . . . " Med. Chem. principle & practice p. 206-208 (1994).*
Patani et al. "Biuoisosterism: a rational approach . . . " Chem. Rev. p. 3147-3176 (1996).*

* cited by examiner

*Primary Examiner*—Celia Chang
(74) *Attorney, Agent, or Firm*—Pepper Hamilton LLP

(57) ABSTRACT

NK2R binding compounds in accord with structural diagram I useful for the treatment or prevention of OAB or UI in mammals, particularly humans are disclosed:

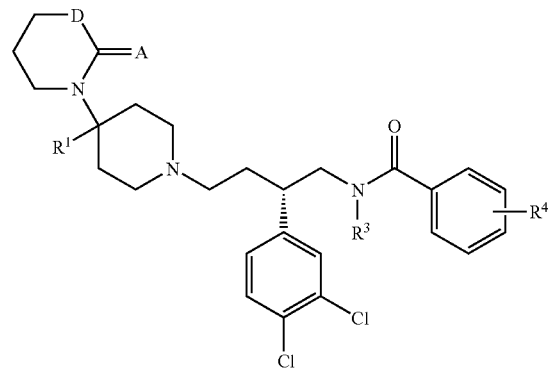

I wherein in said compounds D, A, $R^1$, $R^3$ and $R^4$ are as defined in the specification. Pharmaceutically-advantageous salts of the compounds, methods of use of the compounds, either alone or in combination with other pharmacological agents, and pharmaceutical compositions useful in practicing the methods of the invention are also disclosed.

2 Claims, No Drawings

COMPOUNDS AND METHOD FOR THE TREATMENT OF OVERACTIVE BLADDER

RELATED APPLICATIONS

This is a National Phase filing of International Application PCT/SE02/01991, filed Nov. 1, 2002, which claims the benefit of application Ser. No. 0103795-1, filed in Sweden on Nov. 2, 2001.

FIELD OF THE INVENTION

This invention relates to compounds useful for the treatment and/or prevention of overactive bladder or urinary incontinence, to methods using such compounds and to compositions for the use in the method.

BACKGROUND

Overactive bladder ("OAB") is a term for a syndrome that encompasses urge incontinence, urgency and frequency. Urinary incontinence ("UI") is the involuntary loss of urine that results from an inability of the bladder to retain urine as a consequence of either urge (urge incontinence), or physical or mental stress (stress incontinence).

The normal bladder fills at a physiological rate dictated by the function of the kidneys. The bladder can accommodate large volumes of urine due to the physical properties of the bladder as well as a neural inhibitory system. The inhibitory mechanism is believed to involve inhibition of parasympathetic activity or an increase in sympathetic tone to produce detrusor relaxation and allow filling to occur. During filling the outlet neck of the bladder and urethra are contracted preventing leakage. Voiding or micturition is characterized by a relaxation of the outlet neck and the urethra followed by contraction of the detrusor muscle. When the bladder is empty the detrusor muscle relaxes and the outlet neck and urethra contract to seal off the bladder and maintain continence.

Between 4 and 8% of the total population are estimated to suffer from UI at any point in time, although in most countries, only about 15% of such sufferers are diagnosed. Of those diagnosed only about 70% receive medical treatment. Urge incontinence is more prevalent in the elderly and 80% of the cases are female. Pads and other physical devices are regularly used by a large proportion of incontinent patients not receiving medical treatment. The US market for incontinence pads was estimated at $1.5 billion in 1997.

The muscarinic antagonist oxybutin is prescribed for treatment for OAB in western countries and a second generation muscarinic M3 receptor antagonist, tolterodine, is also marketed for OAB. Propiverine and Flavoxate are prescribed in Japan. Estrogen and progesterone therapy has been studied and is believed to partially alleviate incontinence in some women. Other studies suggest alpha-adrenergic agonists, beta-adrenergic-receptor blocking agents cholinergic receptor-blocking compounds and cholinergic receptor-stimulating drugs may be beneficial. However, existing therapies are associated with side effects including constipation, visual-accommodation abnormalities, xerothalmia (dry eyes) and a "dry mouth" side effect, which is poorly tolerated by some users and therefore, despite the availability of existing treatments, there is a major unmet and growing need for an effective and acceptable medical treatment for UI and OAB.

DESCRIPTION OF THE INVENTION

It has now been discovered that certain compounds that bind to the neurokinin 2 receptor ("NK2R") are useful for the treatment and prevention of overactive bladder ("OAB") and urinary or urethral incontinence ("UI").

In one aspect, certain novel compounds have been discovered that bind to the NK2R receptor useful for the treatment and prevention OAB and UI. Such compounds have a structure in accord with structural diagram I:

wherein,
A is O or S;
D is CH or NH
$R^1$ is H or $C(O)NHR^2$;
$R^2$ is selected from $C_{1-4}$alkyl;
$R^3$ is selected from H or $C_{1-4}$alkyl, and
$R^4$ moieties are selected from halogen, $C_{1-4}$alkyl, $C_{1-4}$alkoxy or cyano,
or a pharmaceutically-acceptable salt thereof
with the proviso that said compound is not (S)—N-[2-(3,4-dichlorophenyl)-4-[4-(2-thio-piperidin-1-yl)piperidino]butyl]-N-methylbenzamide, (S)—N-[2-(3,4-dichlorophenyl)-4-[4-(2-oxo-piperidin-1-yl)-4-carboxyaminoethyl-piperidino]butyl]-N-methylbenzamide, or (S)—N-[2-(3,4-dichlorophenyl)-4-[4-(2-thioperhydro-pyrimidin-1-yl)piperidino]butyl]-N-methylbenzamide.

In another aspect, it has been discovered that compounds useful for the treatment and prevention OAB and UI are those in accord with structural diagram I wherein,
A is O or S;
D is CH or NH
$R^1$ is H or $C(O)NHR^2$;
$R^2$ is selected from $C_{1-4}$alkyl;
$R^3$ is selected from H or $C_{1-4}$alkyl, and
$R^4$ moieties are selected from halogen, $C_{1-4}$alkyl, $C_{1-4}$alkoxy or cyano,
or a pharmaceutically-acceptable salt thereof.

In a more particular aspect compounds wherein A is O, D is CH, $R^1$ is H, $R^3$ is $CH_3$ and $R^4$ is selected from H or halo are useful for the treatment and prevention OAB and UI.

Still more particularly, it has been discovered that compounds in accord with structural diagram I wherein A is O, $R^1$ is $CH_3$ and $R^2$ is fluoro are useful for the treatment and prevention OAB and UI.

Most particular compounds useful for the treatment and prevention OAB and UI are those exemplified herein.

Compounds of the invention possesses NK2R binding properties and certain such compounds selectively inhibit the contraction of bladder tissues. Surprisingly, it has been found that certain compounds in accord with structural diagram I activate the contraction of bladder tissues induced by BANK. One such compound is one wherein A is S, D is NH, $R^1$ is H, $R^3$ is $CH_3$ and $R^4$ is H. Another such compound is one wherein A is O, D is $C(O)NHC_2H_5$, $R^1$ is H, $R^3$ is $CH_3$ and $R^4$ is H.

In one aspect, the Invention provides a method comprising treating or preventing OAB or UI in a subject, particularly in a human, with a compound in accord with structural diagram I and, more particularly, a method that comprises treating with a therapeutically-effective amount of a compound having a structure in accord with structural diagram I.

In a second aspect, the Invention provides a compound of the present invention, for the treatment and prevention of OAB or UI in mammals, and in humans in particular.

In a third aspect, the Invention provides pharmaceutically-acceptable salts of a compound of the present invention and compositions containing said compound or pharmaceutically-acceptable salts thereof.

In a particular aspect, the Invention provides a method comprising treating or preventing OAB or UI in a subject, particularly in a human, with a therapeutically-effective amount of a compound having a structure in accord with structural diagram I that inhibits bladder contractions.

In another aspect, the Invention provides a method for the treatment and prevention of OAB or UI in mammals and humans in particular comprising treating a subject in need thereof with a therapeutically-effective amount of an NK2R binding-compound in combination with another therapeutic agent.

In yet another aspect, the Invention provides a method for the treatment and prevention of OAB or UI in mammals and humans in particular comprising treating a subject in need thereof with a therapeutically-effective amount of an NK2R antagonist in combination with an estrogenic agent and/or a progestational substance, and with or without supplementation with an alpha-adrenergic agonist, beta-adrenergic receptor blocking agent, cholinergic-receptor blocking compound or a cholinergic-receptor-stimulating drug.

In a further aspect, the Invention provides a pharmaceutical composition useful in the practice of the methods of the Invention comprising a compound in accord with structural diagram I and a pharmaceutically-acceptable excipient or diluent.

In all aspects of the invention pharmaceutically-acceptable salts contemplated to be within the scope of the invention are salts such as a hydrochloride, sulphate, tosylate, mesylate, napsylate, besylate, phosphate, salicylate, tartrate, lactate, citrate, benzoate, succinate, fumerate, acetate or a maleate.

It is an object of the Invention to provide a method for the treatment of OAB or UI comprising use of a compound, having a structure in accord with structural diagram I as described heretofore.

It is another object of the Invention to provide a method comprising use of a compound of the present invention for the prevention of OAB or UI.

While the methods of the Invention are applicable to mammals in general they are applicable to humans in particular.

Therefore, it is an object of the Invention to provide a method comprising treating a human patient suffering from OAB or UI and in need of treatment therefore with a therapeutically-effective amount of a compound of the present invention.

Another object of the Invention is to provide a compound in accord with structural diagram I useful for the treatment or prevention of OAB or UI.

A further object of the Invention is to provide pharmaceutically-acceptable salts, compositions, mixtures and the like of said compound useful for the treatment or prevention of OAB or UI.

A particular object of the invention is to provide a method of treating a human patient having OAB or UI, comprising administering an effective OAB or UI treatment amount of a compound having a structure in accord with structural diagram I to the patient.

Another particular object of the invention is to provide a method wherein a compound having a strucure in accord with structural diagram I is in the form of a pharmaceutically-acceptable salt thereof.

In methods of the invention treatment is contemplated to be administered in any physiologically-acceptable manner, such as by topical application, ingestion, inhalation, insufflation or injection.

In methods of the invention a compound of the present invention is contemplated to be in a form such as a capsule, a tablet, an aqueous solution, an aqueous suspension, a non-aqueous suspension, a suppository, an aerosol or a powder.

Treatment of overactive bladder ("OAB") a term generally used, and used herein, for a syndrome that encompasses urinary urge incontinence, urgency and frequency or urinary incontinence ("UI"), the involuntary loss of urine that results from an inability of the bladder to retain urine as a consequence of either urge (urge incontinence), or physical or mental stress (stress incontinence), is an object of the Invention.

Therefore, it is an object of the Invention to provide a method for treating a human patient suffering from OAB or UI.

A particular object of the method of the invention for treating OAB or UI, as contemplated herein, is administration of a therapeutically-effective amount of a compound in accord with structural diagram I.

Another object of the Invention is to provide a compound in accord with structural diagram I useful for the treatment or prevention of OAB or UI.

A further object of the Invention is to provide pharmaceutically-acceptable salts, compositions, mixtures and the like of such a compound useful for the treatment or prevention of OAB or UI.

A particular object of the invention is to provide a method of treating a human patient having OAB or UI comprising administering an effective OAB or UI treatment amount of (S)—N-[2-(3,4-dichlorophenyl)-4-[4-(2-oxoperhydropyrimidin-1-yl)piperidino]butyl]-N-ethylbenzamide to the patient.

Another particular object of the invention is to provide a method wherein (S)—N-[2-(3,4-dichlorophenyl)-4-[4-(2-oxoperhydropyrimidin-1-yl)piperidino]butyl]-N-ethylbenzamide is in the form of a pharmaceutically-acceptable salt thereof.

In methods of the invention treatment is contemplated to be administered by any physiologically-acceptable route for example, by dermal, sublingual, or rectal topical application; by intraperitoneal, parenteral, intradermal or subcutaneous injection; or by ingestion of a capsule, a tablet or a liquid solution or suspension.

Generally, it is contemplated that pharmaceutical compositions of the invention will be formulated so as to permit administration by a physiologically-acceptable route. In methods of the invention compounds are contemplated to be administered in the form such as a capsule, a tablet, an aqueous solution, an aqueous suspension, a non-aqueous suspension, a suppository, an aerosol or a powder.

In certain methods of the invention it is contemplated that compounds will be administered in combination with one or more other therapeutic agents. Such agents are contemplated to be estrogenic agents, progestational substances, alpha-adrenergic agonists, beta-adrenergic-receptor-blocking agents, cholinergic-receptor-blocking agents or cholinergic-receptor-stimulating agents. However, it will be apparent to those of skill in the art that the compounds of the invention can be co-administered with any therapeutic or prophylactic agent and/or medicament or combination thereof that is medically-compatible therewith.

The invention is contemplated to encompass pharmaceutical compositions comprising compounds of the invention together with at least one pharmaceutically-acceptable excipient or diluent.

The invention is also envisioned to encompass pharmaceutical compositions that include agents such as estrogenic agents, progestational substances, alpha-adrenergic agonists, beta-adrenergic-receptor-blocking agents, cholinergic-receptor-blocking agents or cholinergic-receptor-stimulating agents.

Pharmaceutical compositions contemplated to fall within the scope of the invention include those having forms such as capsules, tablets, aqueous solutions, aqueous suspensions, non-aqueous suspensions, suppositories, aerosols and powders.

Further aspects, objects and advantages of this Invention will become apparent to those skilled in the art upon study of the specification and the appended claims.

However, it will be appreciated that when used in the treatment of OAB, UI or related disease, a compound of the Invention is contemplated to be administered as an appropriate pharmaceutical composition which comprises a compound of the Invention or a pharmaceutically-acceptable salt of the Compound, such as a chloride, sulphate, tosylate, mesylate, napsylate, besylate, phosphate, salicylate, tartrate, lactate, citrate, benzoate, succinate, acetate, maleate, or the like, together with a pharmaceutically-acceptable diluent or carrier. Such salts are prepared by methods known to those of skill in the art. The form of a pharmaceutical composition is adapted for the particular route of administration chosen. Such forms include, for example, tablets, capsules, solutions or suspensions for oral administration; solutions or suspensions for topical administration; suppositories for rectal administration; sterile solutions or suspensions for administration by intravenous or intramuscular infusion or injection; aerosols or nebulizer solutions or suspensions for administration by inhalation; or powders together with pharmaceutically-acceptable solid diluents such as lactose for administration by insufflation.

For oral administration a tablet or capsule containing therapeutically-effective amount from 0.1 mg up to 250 mg (and typically 5 to 100 mg) of a compound of the Invention may conveniently be used. For administration by inhalation, a compound of the Invention will be administered to humans in a daily dose range of, for example, 5 to 100 mg, in a single dose or divided into two to four daily doses. Similarly, for intravenous or intramuscular injection or infusion a sterile solution or suspension containing up to 10% w/w (and typically 0.05 to 5% w/w) of a compound of the Invention may conveniently be used.

The dose of a compound of the Invention to be administered will necessarily be varied according to principles well known in the art, taking account of the route of administration and the severity of the condition and the size and age of the patient under treatment. General, it is contemplated that a compound of the Invention will be administered as a dose within the range of about 0.01 to about 25 mg/kg, and more particularly as a dose within the range 0.1 to 5 mg/kg. It will be understood that generally equivalent amounts of an N-oxide or a pharmaceutically-acceptable salt or a quaternary ammonium salt of a compound of the Invention may be used.

EXAMPLES

As used herein, unless stated otherwise:

(i) temperatures are given in degrees Celsius ("° C."); operations were carried out at room or ambient temperature, that is, at a temperature in the range of 18-25° C.;

(ii) organic solutions were dried over anhydrous $MgSO_4$; evaporation of solvent was carried out using a rotary evaporator under reduced pressure (600-4000 pascals; 4.5-30 mm Hg) with a bath temperature of up to 60° C.;

(iii) chromatography, means flash chromatography; reversed phase chromatography, means flash chromatography over octadecylsilane ("ODS") coated support having a particle diameter of 32-74μ, known as "PREP-40-ODS" (Art 731740-100 from Bodman Chemicals, Aston, Pa., USA); Thin layer chromatography ("TLC") was carried out on silica gel plates;

(iv) in general, the course of reactions was followed by TLC and reaction times are given for illustration only;

(v) melting points are uncorrected and "dec" indicates decomposition; the melting points given are those obtained for the materials prepared as described; polymorphism may result in isolation of materials with different melting points in some preparations;

(vi) final products had satisfactory proton nuclear magnetic resonance ("NMR") spectra;

(vii) yields are given for illustration only and are not necessarily those which may be obtained by diligent process development; preparations were repeated if more material was required;

(viii) when given, NMR data is in the form of delta values for major diagnostic protons, given in parts per million ("ppm") relative to tetramethylsilane ("TMS") as an internal standard, determined at 300 MHz using perdeuterio dimethyl sulfoxide ("DMSO-d6") as solvent; conventional abbreviations for signal shape are used; coupling constants (J) are given in Hz; Ar designates an aromatic proton when such an assignment is made;

(ix) chemical symbols have their usual meanings; SI units and symbols are used;

(x) reduced pressures are given as absolute pressures in pascals ("Pa"); elevated pressures are given as gauge pressures in bars;

(xi) solvent ratios are given in volume:volume ("v/v") terms; and (xii) LC/MS was detected by a diode ray detector. The analysis was conducted with a Zorbax 50 mm×2.1 mm stable bond C8 analytical column. Solvent A was 0.05% trifluoroacetic acid in water. Solvent B was 90% acetonitrile 9.95% water and 0.05% trifluoroacetic acid. The flow rate was 1.4 mL/minute ramping from 5% B to 90% B in 3 minutes. Retention times are given in minutes. The ionization method was APCI, or atmospheric pressure chemical ionization. Generally, only ions which indicate the parent ions are reported.

CHEMICAL EXAMPLES

Example 1

(S)—N-[2-(3,4-Dichloro-phenyl)-4-(2-oxo-[1,4']bipiperidinyl-1'-yl)-butyl]-2-fluoro-N-methyl-benzamide To solution of (S)-1'-[3-(3,4-dichloro-phenyl)-4-methylamino-butyl]-[1,4']bipiperidinyl-2-one (0.3 g) in dichloromethane (7 mL) at 0° C. was added 2-fluorobenzoyl chloride neat. After 45 minutes at ambient temperature, the solution was washed with aqueous sodium bicarbonate, dried and evacuated to an oil which was purified with chromatography, eluting with methanol:dichloromethane (gradient 3:97, 6:94). Concentration to a viscous oil under high vacuum provided the title compound (0.3 g). MS: m/z=534(M+1).

Maleate salt of (S)—N-[2-(3,4-Dichloro-phenyl)-4-(2-oxo-[1,4']bipiperidinyl-1'-yl)-butyl]-2-fluoro-N-methyl-benzamide.

(S)—N-[2-(3,4-Dichloro-phenyl)-4(2-oxo-[1,4']bipiperidinyl-1'-yl)-butyl]-2-fluoro-N-methyl-benzamide (11.7 g) as the free base was taken up in isopropanol (80 mL), mixed with a solution of maleic acid (2.54 g) in isopropanol (80 mL) and heated to just before reflux. The mixture was cooled and stirred overnight at ambient temperature. A resulting solid was filtered and dried under vacuum (crop 1, 10.2 g). Crop 1 was taken up in isopropanol (250 mL) and refluxed until it was in solution, then stirred at ambient temperature overnight. A solid precipitate was filtered and dried under high vacuum (crop 2, 7.1 g). The mother liquor from crop 1 was evaporated and the residue taken up in isopropanol (50 mL) and stirred over night. Formed crystals were filtered and dried under vacuum (crop 3, 1.7 g). Crop 1 and crop 3 were both highly hygroscopic. Crop 1 and crop 3 were dissolved in ethanol (80 mL) with heating and were stirred overnight at ambient temperature. No crystals were evident the next day. Diethyl ether was added diluting to a total volume of 500 mL. After 15 minutes a solid began to appear. After 5 hours the solid was filtered, washing with 50:50 diethyl ether:ethanol, and dried under high vacuum at 65° C. (7.5 g). MS: m/z=534(M+1). Analysis for C28H34Cl2FN3O2 1.0 C4H4O4 0.1 H2O: Calculated: C, 58.92; H, 5.902; N, 6.44; Found: C, 58.35-58.54, H 5.51-5.47, N 6.38-6.41.

The intermediate (S)-1'-[3-(3,4-dichloro-phenyl)-4-methylamino-butyl]-[1,4']bipiperidinyl-2-one was prepared as follows.

1a. (S)-[2-(3,4-Dichloro-phenyl)-4-hydroxy-butyl]-methyl-carbamic acid tert-butyl ester To a solution of 3-(3,4-dichloro-phenyl)-4-methylamino-butan-1-ol (25.0 g) in dichloromethane (125 mL) was added di-tert-butyl dicarbonate dropwise as a solution in dichloromethane (125 mL). After stirring for 3 hours, the reaction mixture was washed with dilute hydrochloric acid, dilute sodium bicarbonate, dried, and evaporated. A resulting oil was chromatographed eluting with dichloromethane:ether (2:1).

1b. (S)-[2-(3,4-Dichloro-phenyl)-4-oxo-butyl]-methyl-carbamic acid tert-butyl ester To a solution of oxalyl chloride (2.84 mL) in dichloromethane (70 mL) at −78° C. was added dimethylsulfoxide (4.6 mL) in dichloromethane (35 mL). This mixture was stirred for about 7 minutes at −78° C. before (S)-[2-(3,4-dichloro-phenyl)-4-hydroxy-butyl]-methyl-carbamic acid tert-butyl ester (9.1 g) was added as a solution in dichloromethane (25 mL). This mixture was stirred at −78° C. for 30 minutes before triethylamine (18.1 mL) was added neat. The mixture was then stirred for 30 minutes at −78° C., 45 minutes at 0° C., then warmed to ambient temperature. The solution was diluted with dichloromethane, washed with dilute hydrochloric acid, aqueous sodium bicarbonate, dried and evaporated. MS: m/z=346(M+1). The product was used with no further purification.

1c. (S)-[2-(3,4-Dichloro-phenyl)-4-(2-oxo-[1,4']bipiperidinyl-1'-yl)-butyl]-methyl-carbamic acid tert-butyl ester To a solution of [1,4']bipiperidinyl-2-one (4.5 g) in methanol (100 mL) was added acetic acid (1.49 mL). The solution was stirred for several minutes before (S)-[2-(3,4-dichloro-phenyl)-4-oxo-butyl]-methyl-carbamic acid tert-butyl ester (26 mmole) was added in methanol (25 mL). Stirring was continued for 20 minutes after which time, sodium cyanoborohyuride (1.64 g) was then added in methanol (5 mL). The mixture was stirred for two days and then diluted with aqueous sodium bicarbonate and concentrated. It was then partitioned between layers of water and dichloromethane. The aqueous layers were washed with dichloromethane and the organic phases were combined, dried and evacuated to viscous oil which was purified by flash chromatography eluting with methanol:dichloromethane (5:95). This material formed a white foam upon drying under vacuum (9.4 g). MS: m/z=512(M+1).

1d. (S)-1'-[3-(3,4-Dichloro-phenyl)-4-methylamino-butyl]-[1,4']bipiperidinyl-2-one Trifluoroacetic acid (13.1 mL) was added to a solution of (S)-[2-(3,4-dichloro-phenyl)-4-(2-oxo-[1,4']bipiperidinyl-1'-yl)-butyl]-methyl-carbamic acid tert-butyl ester (8.73 g) in dichloromethane (300 mL). After stirring for 30 minutes additional trifluoroacetic acid (13.1 mL) was added. After 1.5 hours the reaction was diluted with aqueous sodium hydroxide, and the layers were separated. The organic layer was washed with water, dried and evacuated to a viscous oil which was not purified further. MS: m/z=412(M+1).

Example 2

(S)—N-[2-(3,4-Dichlorophenyl)-4-[4-(2-thio-piperidin-1-yl)piperidino]butyl]-N-methylbenzamide (S)—N-[2-(3,4-Dichlorophenyl)-4-oxobutyl]-N-methylbenzamide (0.50 g) in methanol (2 mL) was added to a solution of [1,4']bipiperidinyl-2-thione (0.34 g) and acetic acid (0.10 mL) in methanol (6 mL). After 5 minutes, sodium cyanoborohydride (0.108 g) in methanol (2 mL) was added in a single portion. After being stirred overnight, the reaction mixture was diluted with saturated aqueous sodium bicarbonate, stirred for 30 minutes, and extracted with dichloromethane (3×50 mL). The organic extracts were dried, evaporated, and purified by chromatography, with dichloromethane:methanol (gradient 98:2, 95:5) as eluent. The resulting material was dissolved in dichloromethane, precipitated as the hydrochloride salt with ethereal hydrogen chloride, evaporated, and placed under high vacuum overnight to give the title compound as a white solid (0.490 g). MS: m/z=532(M+).

The intermediate, [1,4']bipiperidinyl-2-thione, was prepared as follows:

2a. 4-(5-Chloro-pentanoylamino)-piperidine-1-carboxylic acid benzyl ester

4-Amino-piperidine-1-carboxylic acid benzyl ester (12.0 g) in dichloromethane (100 mL) was added to pyridine (7.2 mL). The solution was cooled to 0° C. then 5-chlorovaleryl chloride (7.3 g) was added drop wise to the reaction. The reaction was warmed to room temperature. After 5 hours the reaction was diluted with dichloromethane and washed with water (1×), saturated aqueous copper sulfate (2×), and water (1×). The organic extracts were dried and evaporated. The resulting solids were suspended in ether, filtered, and then placed under high vacuum to give the title compound as a white solid (15.6 g). $R_f$=0.60 in ethyl acetate.

2b. 2-Oxo-[1,4']bipiperidinyl-1'-carboxylic acid benzyl ester 4-(5-Chloro-pentanoylamino)-piperidine-1-carboxylic acid benzyl ester (15.6 g) was added to a suspension of sodium hydride (2.12 g) in tetrahydrofuran (175 mL). After being stirred overnight, the reaction was quenched with water, then the tetrahydrofuran was removed under reduced pressure. The aqueous solution was diluted with water and extracted with methylene chloride (4×50 mL). The organic extracts were dried and evaporated to give the title compound (15 g). $R_f$=0.30 in ethyl acetate. MS: m/z=317 (M+H).

2c. 2-Thioxo-[1,4']bipiperidinyl-1'-carboxylic acid benzyl ester

2-Oxo-[1,4']bipiperidinyl-1'-carboxylic acid benzyl ester (3.1 g) in tetrahydrofuran (10 mL) was added to a suspension of Lawesson's Reagent (1.98 g) in tetrahydrofuran (40 mL). After 20 minutes the reaction was concentrated and the resulting gum was subjected to chromatography with methylene chloride: ether (gradient 10:1, 5:1) as eluent. The title compound was obtained as a white foam (2.9 g). $R_f$=0.42 in methylene chloride:ether (10:1). MS: m/z=333 (M+H).

2d. [1,4]Bipiperidinyl-2-thione

Anisole (2.5 mL) was added to a solution of 2-thioxo-[1, 4']bipiperidinyl-1'-carboxylic acid benzyl ester (2.4 g) in methylene chloride (40 mL) at 0° C. followed by the addition of trifluorosulfonic acid (3.4 mL). After 30 minutes, solid potassium carbonate was added, then sodium sulfate and methanol. The solids were removed by filtration and the filtrate was concentrated. The residue was dissolved in methanol and neutralized by passage through a column of Amberlyst A-21 (slightly basic) resin. The filtrate was collected and concentrated and purified by chromatography, with methylene chloride:methanol (gradient 95:5, 90:10) as eluent. The title compound was obtained as a white solid (0.93 g). MS: m/z=199 (M+H).

Example 3

(S)—N-[2-(3,4-Dichlorophenyl)-4-[4-(2-oxo-piperidin-1-yl)piperidino]butyl]-N-methyl-3-fluorobenzamide 3-Fluorobenzoyl chloride (0.088 mL) was reacted with (S)-1'-[3-(3,4-dichloro-phenyl)-4-methylamino-butyl]-[1,4'] bipiperidinyl-2-one (0.30 g) in dichloromethane (78 mL) overnight. The reaction was diluted with dichloromethane and washed with saturated aqueous sodium bicarbonate. The organic extracts were dried, evaporated, and purified by chromatography, with dichloromethane:methanol (gradient 97:3, 94:6) as eluent to give the title compound (0.28 g). $R_f$=0.36 in methylene chloride:methanol (95:5). MS: m/z=534 (M+). The product was dissolved in methanol (2 mL) and citric acid was added. The solution was concentrated and the residue was triturated with ether. The product was obtained as a white foam (0.093 g).

The intermediate, (S)-1'-[3-(3,4-dichloro-phenyl)-4-methylamino-butyl]-[1,4']bipiperidinyl-2-one, was prepared as described in Example 1.

Example 4

(S)—N-[2-(3,4-Dichlorophenyl)-4-[4-(2-oxo-piperidin-1-yl)piperidino]butyl]-N-methyl-4-fluorobenzamide 4-Fluorobenzoyl chloride (0.093 mL) was reacted with (S)-1'-[3-(3,4-dichloro-phenyl)-4-methylamino-butyl]-[1,4'] bipiperidinyl-2-one (0.325 g) in dichloromethane (8 mL) overnight. The reaction was diluted with dichloromethane and washed with saturated aqueous sodium bicarbonate. The organic extracts were dried, evaporated, and purified by chromatography, with dichloromethane:methanol (gradient 97:3, 94:6) as eluent to give the title compound (0.33 g). $R_f$=0.41 in methylene chloride:methanol (95:5). MS: m/z=534 (M+). The product was dissolved in methanol (2 mL) and citric acid was added. The solution was concentrated and the residue was triturated with ether. The product was obtained as a white foam(0.11 g).

The intermediate, (S)-1'-[3-(3,4-dichloro-phenyl)-4-methylamino-butyl]-[1,4']bipiperidinyl-2-one, was prepared as described in Example 1.

Example 5

(S)—N-[2-(3,4-Dichlorophenyl)-4-[4-(2-oxo-piperidin-1-yl)piperidino]butyl]-N-methylbenzamide (S)—N-[2-(3,4-Dichlorophenyl)-4-oxobutyl]-N-methylbenzamide (0.78 g) in methanol (3 mL) was added to a solution of [1,4']bipiperidinyl-2-one (0.34 g) and acetic acid (0.15 mL) in methanol (8 mL). After 10 minutes, sodium cyanoborohydride (0.17 g) in methanol (4 mL) was added in a single portion. After being stirred overnight, the reaction mixture was diluted with saturated aqueous sodium bicarbonate, stirred for 30 minutes, and extracted with dichloromethane (4×50 mL). The organic extracts were dried, evaporated, and purified by chromatography, with dichloromethane:methanol (gradient 95:5, 90:10) as eluent to give the title compound (0.95 g). MS: m/z=516(M+). The product was dissolved in methanol (2 mL) and citric acid was added. The solution was concentrated and the residue was triturated with ether. The product was obtained as a white foam (1.2 g).

The intermediate, [1,4']bipiperidinyl-2-one, was prepared as follows:

5a. [1,4']Bipiperidinyl-2-one

2-Oxo-[1,4']bipiperidinyl-1'-carboxylic acid benzyl ester (2.5 g) and Pearlman's catalyst (0.50 g) was stirred in ethanol (30 mL) under hydrogen (1 atm). After 20 hours the reaction as filtered through celite and concentrated. The title compound was obtained as a white solid (1.45 g). MS: m/z=183 (M+H).

5b. (S)—N-[2-(3,4-Dichlorophenyl)-4-oxobutyl]-N-methylbenzamide

To a solution of oxalyl chloride (4.5 ml) in dichloromethane (100 mL) at −78° C., dimethylsulfoxide (7.4 mL) in dichlororomethane (40 mL) was added. After the addition was complete, the solution was stirred for another 30 minutes at −78° C. A solution of (S)—N-[2-(3,4-dichlorophenyl)-4-hydroxy-butyl]-N-methyl-benzamide (14.6 g) in dichloromethane (35 mL) and dimethylsulfoxide (7 ml) was then added drop wise. The solution was stirred at −78° C. for one hour. Triethylamine (29 mL) was added drop wise to the reaction and after 20 minutes the ice bath was removed and the solution was stirred at ambient temperature for 30 minutes. The reaction mixture was diluted with dichloromethane (200 mL), and washed with dilute aqueous hydrochloric acid (150 mL), water (150 mL), and aqueous sodium bicarbonate (150 mL). The separated organic layer was dried and evaporated then dissolved in ether. The white precipitate that formed, was filtered and dried giving the title compound (9.1 g). $R_f$=0.41 methylene chloride:methanol (95:5).

Example 6

(S)—N-[2-(3,4-Dichlorophenyl)-4-[4-(2-oxo-piperidin-1-yl)-4-carboxyaminoethyl-piperidino]butyl]-N-methylbenzamide A solution of 1-benzyloxycarbonyl-4-carboxy-4-(2-oxopiperidino)piperidine (1.45 g), ethylamine hydrochloride (0.32 g), 4-(dimethylamino)-pyridine (0.59 g), triethylamine (0.67 mL), and 1-(3-dimethylaminopropyl)-3-ethylcarbodiimide hydrochloride (0.92 g) in dichloromethane (20 mL) was stirred overnight. The reaction mixture was diluted with dichloromethane and washed successively with 1.0 N hydrochloric acid, saturated aqueous sodium bicarbonate, and water. The separated organic layer was dried and evaporated to give the title compound (1.37 g) as a white solid which did not require purification; NMR: 7.35 (m,5), 6.71 (m,1), 5.12 (s,2), 3.56 (m,4), 3.28 (m,$^4$), 2.43 (m,2), 2.27 (m,2), 2.20 (m,2), 1.76 (m,4), 1.11 (t,3, J=7.2).

The action of a compound of the Invention as a therapeutic agent for the treatment of OAB or UI through its action to bind to NK2 receptors has been shown using suitably designed in vitro and in vivo tests.

In Vitro Binding Assay

Preparation of Membranes from MEL Cells Transfected with Cloned Human NK1 or NK2 receptors:

The cloning of the human lung NK1 and NK2 receptors was achieved as described by Hopkins, et al., Biochem. Biophys. Res. Commun. 180: 1110-1117 (1991), and Graham, et al., Biochem. Biophys. Res. Commun. 177: 8-16 (1991). Heterologous expression and scale-up growth of MEL cells transfected with human tachykinin receptors was performed as described for NK2 receptors by Aharony, et al., Mol. Pharmacol. 45: 9-19, 1994.

Membranes from recombinant MEL cells expressing NK1 or NK2 receptors were prepared as described by Hopkins, et al., (1991). Briefly, cells were homogenized at 4° C. (Brinkman PT-20 Polytron, setting 3, with one 15 sec burst on ice), in a buffer consisting of 50 mM Tris-HCl (pH7.4), 5 mM KCl, 120 mM NaCl, 10 mM EDTA and containing several protease inhibitors (1 mM phenylmethylsulfonylfluoride; 0.1 mg/ml soybean trypsin inhibitor, and 1 mM iodoacetamide). The homogenate was centrifuged at 1200×g for 45 min at 4° C. to remove cell debris. The supernatant was centrifuged at 48,000×g for 45 min at 4° C. The pellet was resuspended with a glass-Teflon motorized homogenizer in 30 volumes of ice-cold 50 mM Tris-HCl (pH 7.4) buffer.

Receptor Binding Assays:

Ligand binding assays with [$^3$H]NKA in MEL cells expressing cloned NK2 receptors or [$^3$H]SP in MEL cells expressing cloned NK1 receptors, were conducted generally as described by Aharony, et al., Mol. Pharmacol. 45: 9-19, 1994, Aharony, et al., Neuropeptides 23: 121-130 (1992) and Aharony, et al., J. Pharmacol. Exp. Ther. 259: 146-155 (1991). In brief, incubations were carried out in assay buffer containing membranes, test compounds, and [$^3$H] ligand (1.0-1.5 nM). In competition experiments, mixtures (0.315 mL) containing various concentrations of competing agents (agonists, antagonists, or vehicle), were incubated at 25° C. for 30 min., with or without 1 μM unlabeled homogenous ligand (NKA or SP), to define non-specific binding. Reactions were initiated by adding membranes (0.1-0.15 mg protein/final concentration) and were conducted in duplicate. Saturation and kinetic experiments were conducted in triplicate. Separation of receptor-bound and free ligand was accomplished by dilution with 1 mL of wash buffer (20 mM Tris-HCl, pH 7.5) followed immediately by vacuum filtration with a total volume of 10 mL of wash buffer (utilizing a Brandel Cell Harvester MB-48R with Whatman GF/B filters presoaked in 0.1% polyethylenimine).

The ability of compounds disclosed herein to inhibit the binding of [$^3$H] ligand is shown by the results disclosed in Table 1.

In Vivo Assay:

BANK-Induced Bladder Contraction in Anesthetized Guinea Pigs:

Female guinea pigs (300-450 g) were anesthetized by intramuscular administration of ketamine/xylazine mixture (3/10 mg/kg, respectively). The jugular vein was catheterized and the distal end of the catheter connected to a syringe for administration of compound where appropriate. Subsequently, the bladder was exposed through a midline abdominal incision, the ureters tied with 4-0 silk suture approximately 2 cm above the bladder, and cut above the ligature to allow drainage from the kidneys. Cannula were passed through the proximal urethra and bladder sphincter into the bladder lumen. The bladder was manually emptied, infused with 0.3 mL saline, and the catheter attached to a Gould p23 ID pressure transducer for recording changes in bladder pressure. An equilibration period of approximately 15 min was allowed for stabilization of the animals following surgical preparation. Thiorphan (10 mg/kg iv) was administered 15 minutes before agonist exposure to inhibit neutral endopeptidase 3.4.24.11.

The response was allowed to decay during a 15 min equilibration period before intravenous administration of test compound (0.2-5 mmol/kg, 5% PEG 400-saline vehicle). An additional 15 min equilibration period elapsed before administration of an equivalent dose of BANK was repeated. Preliminary studies were performed to establish equivalence of bladder contractile responses to multiple administrations of BANK. Effects were calculated as the percentage difference between the response to BANK in the presence and absence of test compounds.

To establish the oral effect of test compounds, animals were administered the test compounds (52 nmol/kg, 5% PEG 400-saline vehicle) by gavage 1 hr before administration of BANK. This was followed by intravenous administration of BANK (3 nmol/kg). Bladder contraction occurring in the presence or absence of test compound was recorded as an increase in intravesical bladder pressure on a Grass 7D Polygraph and expressed as percent inhibition of the BANK-mediated effect. Duration of action studies were performed following oral administration of test compounds (1.2 mmol/kg, 5% PEG 400-saline vehicle) at different times prior to administration of BANK. Responses were calculated as the percentage difference between the response to BANK in the presence of test compound compared with sham-treated controls. For all studies, each animal was administered a single dose of test compound. Experimental results were expressed as the mean plus or minus the Standard Error of the Mean (±S.E.M) percentage change from basal level.

The ability of compounds disclosed herein to inhibit bladder contractions induced with BANK is shown by the results disclosed in Table 1.

TABLE 1

| Compound of Example: | Inhibition of BANK-mediated GP bladder contraction (% Inhibition mediated by 52 nM/kg administered orally) | hNK2 (Ki expressed as -Log Molar) | hNK1 (Ki expressed as -Log Molar) |
|---|---|---|---|
| 1 | 80 ± 6 | 8.84 | 7.04 |
| 2 | 42 ± 13 | 8.73 | 7.22 |
| 3 | — | — | — |
| 4 | −28 ± 45 | — | — |
| 5 | — | 8.48 | 6.37 |
| 6 | −65 ± 58 | 9.70 | 84% inhibition at 10 μM |

Compounds of the invention are specific for NK2 receptors. Compounds disclosed herein generally exhibit 100 fold or better selectivity for human NK2 receptors as compared to human NK1 receptors, as illustrated by the results shown in Table 1.

Surprisingly, it has been found that compounds with similar binding affinities for human NK2 receptors have different effects when tested for their ability to inhibit bladder contraction induced by BANK. For example, as shown in Table 1, exemplified compounds generally have Ki's of about 9-Log Molar when tested for their ability to inhibit the binding of tritiated NKA to cloned and expressed hNK2 receptors. The compound of Example 1 however is found to provide an 80% inhibition of BANK induced bladder contraction whereas, unexpectedly, the compound of Example 4 is found to provide a 28% increase in the bladder contraction induced by BANK.

Compounds of the Invention have not been found to show any indication of any untoward side-effects in laboratory test animals at several multiples of the minimum effective dose.

The invention claimed is:

1. A compound which is (S)-N-[2-(3,4-dichlorophenyl)-4-[4-(2-oxo-piperidin-1-yl)piperidino]butyl]-N-methyl-2-fluorobenzamide, or a pharmaceutically-acceptable salt thereof.

2. A pharmaceutical composition comprising (S)-N-[2-(3,4-dichlorophenyl)-4-[4-(2-oxo-piperidin-1yl)piperidino]butyl]-N-methyl-2-fluorobenzamide or a pharmaceutically-acceptable salt thereof and at least one pharmaceutically-acceptable excipient or diluent.

* * * * *